US012778392B2

(12) United States Patent
Zhang et al.

(10) Patent No.: US 12,778,392 B2
(45) Date of Patent: Nov. 3, 2026

(54) ADJUSTMENT DEVICE AND MEDICAL SYSTEM

(71) Applicants: Ankon Medical Technologies (Shanghai) Co., LTD., Shanghai (CN); ANX IP HOLDING PTE. LTD., SG (SG)

(72) Inventors: Shaobang Zhang, Shanghai (CN); Yueyue Shen, Shanghai (CN); Hongtao Zhang, Shanghai (CN)

(73) Assignees: ANKON MEDICAL TECHNOLOGIES (SHANGHAI) CO., LTD, Shanghai (CN); ANX IP HOLDING PTE. LTD., Singapore (SG)

( * ) Notice: Subject to any disclaimer, the term of this patent is extended or adjusted under 35 U.S.C. 154(b) by 992 days.

(21) Appl. No.: 18/011,156

(22) PCT Filed: Jun. 16, 2021

(86) PCT No.: PCT/CN2021/100349

§ 371 (c)(1),
(2) Date: Dec. 16, 2022

(87) PCT Pub. No.: WO2021/254390

PCT Pub. Date: Dec. 23, 2021

(65) Prior Publication Data

US 2023/0172437 A1 Jun. 8, 2023

(30) Foreign Application Priority Data

Jun. 16, 2020 (CN) ........................ 202010546894.X

(51) Int. Cl.
*A61B 1/00* (2006.01)
*F16M 11/04* (2006.01)
(Continued)

(52) U.S. Cl.
CPC ....... *A61B 1/00147* (2013.01); *F16M 11/043* (2013.01); *F16M 11/10* (2013.01); *F16M 13/02* (2013.01); *F16M 2200/021* (2013.01)

(58) Field of Classification Search
CPC ...... F16M 11/043; F16M 11/10; F16M 13/02; F16M 2200/021; A61B 1/00147
(Continued)

(56) References Cited

U.S. PATENT DOCUMENTS 5,855,344 A * 1/1999 Rogers ................ F16M 11/123 248/123.2
6,045,104 A * 4/2000 Nakamura ............ G02B 7/001 248/123.2
(Continued)

FOREIGN PATENT DOCUMENTS

CN 204459649 U 7/2015
CN 207921696 U 9/2018
(Continued)

*Primary Examiner* — Monica E Millner
(74) *Attorney, Agent, or Firm* — Treasure IP Group, LLC

(57) ABSTRACT

An adjustment device and a medical system are for adjusting a medical device. The adjustment device includes a first connection portion for hoisting the adjustment device, a second connection portion is for connecting the medical device, and a locking mechanism. The first connection portion and the second connection portion are rotatably connected through the rotating shaft, so that the first connection portion and the second connection portion rotate relative to each other. The locking mechanism has a locked state and an unlocked state. In the unlocked state, the first connection portion and/or the second connection portion rotate relative to the rotating shaft, to adjust the medical device to a vertical position. In the locked state, the locking mechanism restricts the first connection portion and/or the
(Continued)

second connection portion to rotate relative to the rotating shaft, to maintain the medical device in a vertical state.

18 Claims, 5 Drawing Sheets

(51) Int. Cl.
*F16M 11/10* (2006.01)
*F16M 13/02* (2006.01)

(58) Field of Classification Search
USPC .......................................................... 248/589
See application file for complete search history.

(56) References Cited

U.S. PATENT DOCUMENTS

| | | | | |
|---|---|---|---|---|
| 7,637,466 | B2 * | 12/2009 | Dillard | A61B 90/50 248/280.11 |
| 9,841,660 | B1 * | 12/2017 | Christensen | F16M 11/2014 |
| 10,813,535 | B2 * | 10/2020 | Unai | A61B 1/00149 |
| 11,000,344 | B2 * | 5/2021 | Seo | A61B 90/50 |

FOREIGN PATENT DOCUMENTS

| | | | |
|---|---|---|---|
| CN | 109538899 | A | 3/2019 |
| DE | 102013016369 | A1 | 4/2015 |

* cited by examiner

ADJUSTMENT DEVICE AND MEDICAL SYSTEM

CROSS-REFERENCE OF RELATED APPLICATIONS

The application is a National Phase Application of PCT International Application No. PCT/CN2021/100349, International Filing Date Jun. 16, 2021, which claims priority from Chinese Patent Application No. 202010546894.X, filed Jun. 16, 2020, all of which are incorporated herein by reference in their entireties.

FIELD OF INVENTION

The present invention relates to a medical system, and more particularly, to an adjustment device and a medical system.

BACKGROUND

Medical device that has become an important field of modern healthcare is essential condition for continuously improving level of medical science and technology and is also an important symbol of the degree of modernization. Medical device refers to any instrument, equipment, apparatus, material or other similar or related article that is used independently or in combination for human body.

Typically, a medical device has a series of parts that are connected by a base. A suspended part of the medical device is in a vertical state under the action of gravity. Since the medical device is fixedly connected to the base, the base is required to be at absolute level, which is very difficult to guarantee under normal circumstances. A base that is not absolutely horizontal can cause an overall mechanism connected to the medical device to produce a component force in the vertical direction, thus causing fatigue or even damage to the overall mechanism.

SUMMARY OF THE INVENTION

An adjustment device and a medical system are provided according to the present disclosure, which enable a medical device connected to the adjustment device in a vertical state.

According to one aspect of the present disclosure, an adjustment device, for adjusting a position of a medical device, is provided. The apparatus adjustment device comprises:

- a first connection portion for hoisting the adjustment device;
- a second connection portion for connecting the medical device;
- a rotating shaft, wherein the first connection portion and the second connection portion are rotatably connected r through the rotating shaft, so that the first connection portion and the second connection portion rotate relative to each other; and
- a locking mechanism;
- wherein the locking mechanism comprises a locked state and an unlocked state; in the unlocked state, the first connection portion and/or the second connection portion rotate relative to the rotating shaft, to adjust the medical device to a vertical state; in the locked state, the locking mechanism restricts he first connection portion and/or the second connection portion to rotate relative to the rotating shaft, to maintain the medical device in a vertical state.

In one embodiment, the locking mechanism comprises a limit portion, a first locking portion, and a second locking portion.

One of the first locking portion and the second locking portion is connected to the first connection portion or the second connection portion, and the other is connected to the rotating shaft.

The first locking portion is provided with a holding cavity, and at least part of the second locking portion moves along the holding cavity, so that the locking mechanism is in an unlocked state.

The limit portion is used for limiting a relative movement between the second locking portion and the first locking portion, so that the locking mechanism is in the locked state.

In one embodiment, a side wall of the holding cavity has a through hole.

The second locking portion comprises a plurality of locking grooves in a side facing the through hole, and the plurality of locking grooves are arranged along an axial direction of the second locking portion.

The limit portion extends into the holding cavity through the through hole and fits into the locking groove to limit a relative movement between the second locking portion and the first locking portion.

In one embodiment, the locking mechanism further comprises a valve, and a stem of the valve is the limit portion.

In one embodiment, the side wall of the holding cavity comprises a recess, and the recess extends in length along an axial direction of the first locking portion.

The second locking portion comprises a protrusion, at least part of the protrusion is located in the recess and moves in the recess, and two side walls of the recess along the axial direction of the first locking portion are for limiting a distance of movement of the protrusion.

In one embodiment, along the axial direction of the first locking portion, a size of the recess is less than or is equal to a length of arrangement of the plurality of locking grooves.

In one embodiment, the rotating shaft comprises at least a first rotating shaft and a second rotating shaft, and the first rotating shaft and the second rotating shaft are perpendicular to and connected to each other.

The first connection portion is rotatably connected to the first rotating shaft, and the second connection portion is rotatably connected to the second rotating shaft.

In one embodiment, the locking mechanism is disposed between the first connection portion and the second rotating shaft.

Two ends of the locking mechanism are rotatably connected to the first connection portion and the second rotating shaft, respectively.

When the locking mechanism is in the locked state, the second connection portion is restricted from rotating about the first rotating shaft, and when the locking mechanism is in the unlocked state, the second rotating shaft rotates relative to the first connection portion to allow the second connection portion to rotate about the first rotating shaft.

In one embodiment, the locking mechanism is disposed between the second connection portion and the first rotating shaft.

Two ends of the locking mechanism are rotatably connected to the second connection portion and the first rotating shaft, respectively.

When the locking mechanism is in the locked state, the second connection portion is restricted from rotating about the second rotating shaft, and when the locking mechanism is in the unlocked state, the second connection portion rotates relative to the first rotating shaft to allow the second connection portion to rotate about the second rotating shaft.

In one embodiment, the first rotating shaft, the second rotating shaft, the first connection portion and the second connection portion are all connected to hinge bases, and the corresponding locking mechanisms corresponding to the first rotating shaft, the second rotating shaft, the first connection portion and the second connection portion are rotatably connected to the hinge bases.

According to another aspect of the present disclosure, a medical system is provided, comprises:

a medical device; and an adjustment device, is the same as described above.

wherein the adjustment device is connected to the medical device for adjusting a position of the medical device.

In accordance with the present disclosure, the adjustment device can adjust the position of the medical device to make the medical device in a vertical state and lock it to maintain the vertical state to avoid rotation by external thrust.

It should be understood that the above description and the details to be set forth in the following text are only exemplary, which are not intended to limit the invention.

MARKS IN THE DRAWINGS

Figure 1:
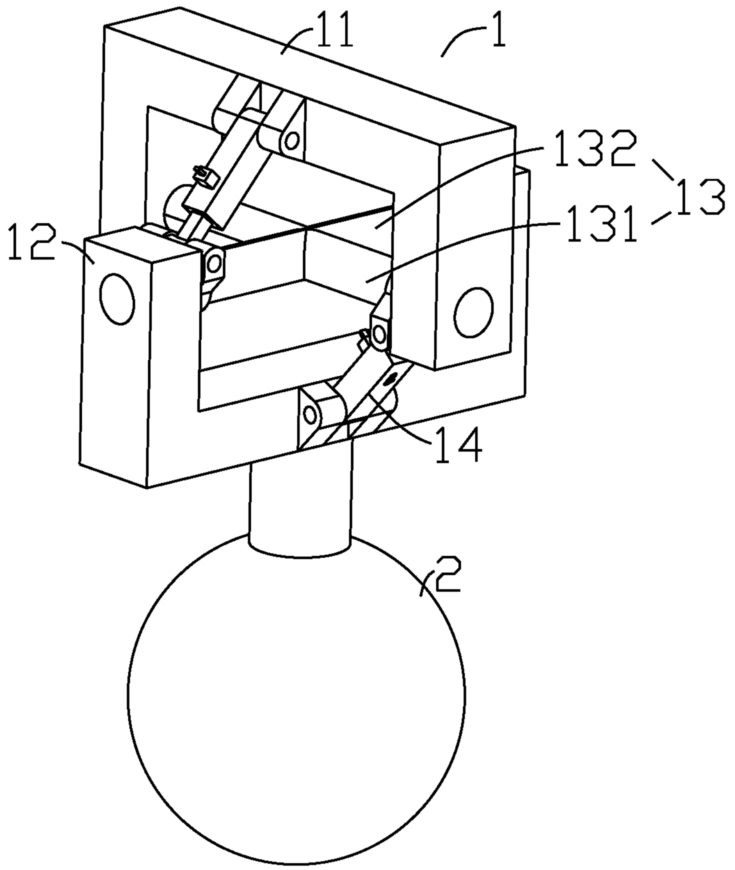
FIG. 1 shows a structure of an adjustment device in accordance with an embodiment of the present invention.

1—Adjustment device;
- 11—First connection portion;
- 12—Second connection portion;
- 13—Rotating shaft;
  - 131—First rotating shaft;
  - 132—Second rotating shaft;
- 14—Locking mechanism;
  - 141—Limit portion;
  - 142—First locking portion;
    - 142*a*—Holding cavity;
      - 142*a*1—Through hole;
      - 142*a*2—Recess;
  - 143—Second locking portion;
    - 143*a*—Locking groove;
    - 143*b*—Protrusion;
  - 144—Valve;
- 15—Hinge base;

2—Medical device.

The drawings herein are incorporated in and constitute a part of the specification, illustrate the embodiments consistent with the present invention and are used together with the specification to explain the principles of the present invention.

DETAILED DESCRIPTION

In order to better understand technical solutions of the present application, embodiments of the present application are described in detail below in conjunction with the accompanying figures.

It should be clear that the embodiments described are only a portion of the embodiments of the present application. Based on the embodiments in the present application, all other embodiments obtained by a person of ordinary skill in the art without creative labor fall within the scope of protection of the present application.

In one specific embodiment, the present application is described in further detail below by way of specific embodiments and in conjunction with the accompanying figures.

Medical device that has become an important field of modern healthcare is essential condition for continuously improving level of medical science and technology and is also an important symbol of the degree of modernization. The development of medical field depends to a large extent on the development of instruments, and even in the development of the medical industry, its breakthrough bottleneck also plays a decisive role. Medical device refers to any instrument, equipment, apparatus, material or other similar or related article that is used independently or in combination for human body. The medical device can be a diagnostic equipment, a therapeutic equipment or an auxiliary equipment, such as a magnetic control capsule endoscope equipment.

A medical device has a series of parts that are connected to each other through a base, for example, a suspended part of the medical device in a vertical state under the action of gravity. Since some medical devices are fixedly connected to the base, the base is required to be at absolute level, which is very difficult to guarantee under normal circumstances. A base that is not absolutely horizontal can cause an overall mechanism connected to the medical device to produce a component force in the vertical direction, thus causing fatigue or even damage to the overall mechanism.

Referring to FIGS. 1-7, in accordance with some embodiments of the present disclosure, a medical system is provided. The medical system comprises a medical device 2 and an adjustment device 1. The adjustment device 1 is detachably connected or fixedly connected to the medical device 2, and is used to adjust a position of the medical device 2 so as to make the medical device in a vertical state. The medical device 2 may be an X-ray diagnostic equipment, an ultrasonic diagnostic equipment, a functional inspection equipment, an endoscopy equipment, a nuclear medicine equipment, a laboratory diagnostic equipment, a pathological diagnostic equipment, and a magnet of an endoscopic control equipment, etc. The adjustment device 1 comprises a first connection portion 11, a second connection portion 12, a rotating shaft 13, and a locking mechanism 14. The first connection portion 11 is used for hoisting the adjustment device 1, that is, when the adjusting device 1 is installed to a mounting base, the first connecting part 11 of the adjusting device 1 can be hoisted to the mounting base to lift the adjusting device 1 to the mounting base. The second connection portion 12 is used for connecting the medical device 2, and the first connection portion 11 and the second connection portion 12 are rotatably connected through the rotating shaft 13, so that the first connection portion 11 and the second connection portion 12 can rotate relative to each other, and a position of the medical device 2 connected to the second connecting section 12 can be adjusted during the relative rotation of the first connection portion 11 and the second connection portion 12.

The locking mechanism 14 comprises a locked state and an unlocked state. When the locking mechanism 14 is in the unlocked state, the first connection portion 11 and/or the second connection portion 12 can rotate relative to the rotating shaft 13, so as to adjust the medical device 2 to a vertical position. When the locking mechanism 14 is in the locked state, the locking mechanism 14 restricts the first connection portion 11 and/or the second connection portion 12 to rotate relative to the rotating shaft 13, to maintain the medical device 2 in a vertical state and prevent the medical device 2 from being in a tilted state after being connected to the base, thus ensuring structural stability of the overall mechanism of the medical device 2.

In the embodiments of the present invention, the vertical state of the medical device 2 is a state in which the medical device 2 is perpendicular to a ground. Specifically, when the medical device 2 is connected to the second connection portion 12, the line between a connection point of the medical device 2 and the second connection portion 12 and a center of gravity of the medical device 2 is perpendicular to the ground, or the line between the connection point of the medical device 2 and the second connection portion 12 and the center of gravity of the medical device 2 is parallel to the gravity of the medical device 2. If the medical device 2 is not in the vertical state, the locking mechanism 14 is controlled to unlock, and the medical device 2 with its own gravity drives the second connection portion 12 to rotate and adjust the medical device 2 to the vertical state. After the medical device 2 is adjusted to the vertical state, the locking mechanism 14 is controlled to lock to maintain the vertical state and avoid rotating about the rotating shaft 13 by an external thrust. Also, the risk of fatigue work or even damage to the medical device 2 caused by component forces in other directions can be reduced when the medical device 2 is tilted.

Further, in a preferred embodiment of the present invention, the first connection portion 11 and the second connection portion 12 may be arranged in a U-shaped structure. The first connection portion 11 is located above the second connection portion 12, and the first connection portion 11 and the second connection portion 12 are vertically arranged. The openings of the first connection portion 11 and the second connection portion 12 are arranged opposite to each other, and the rotating shaft 13 is located in a space enclosed by the first connection portion 11 and the second connection portion 12 and is rotatably connected to the first connection portion 11 and the second connection portion 12. Alternatively, the first connection portion 11 and the second connection portion 12 may also be in other structural forms, as long as it can ensure that the second connection portion 12 can rotate relative to the first connection portion 11 and adjust the medical device 2 to the vertical state, which are not be repeated here.

Figure 2:
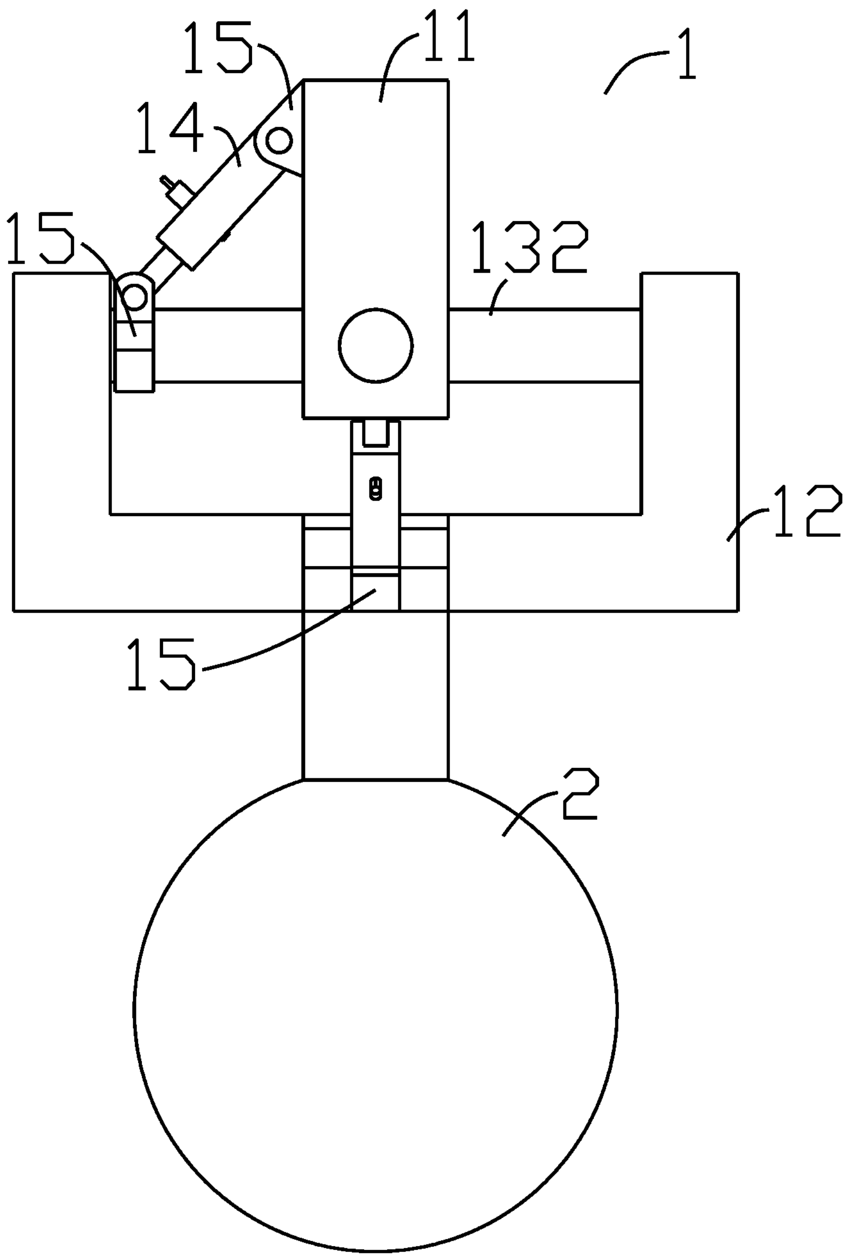
FIG. 2 shows the structure as shown in FIG. 1 from other viewing angle.
Figure 3:
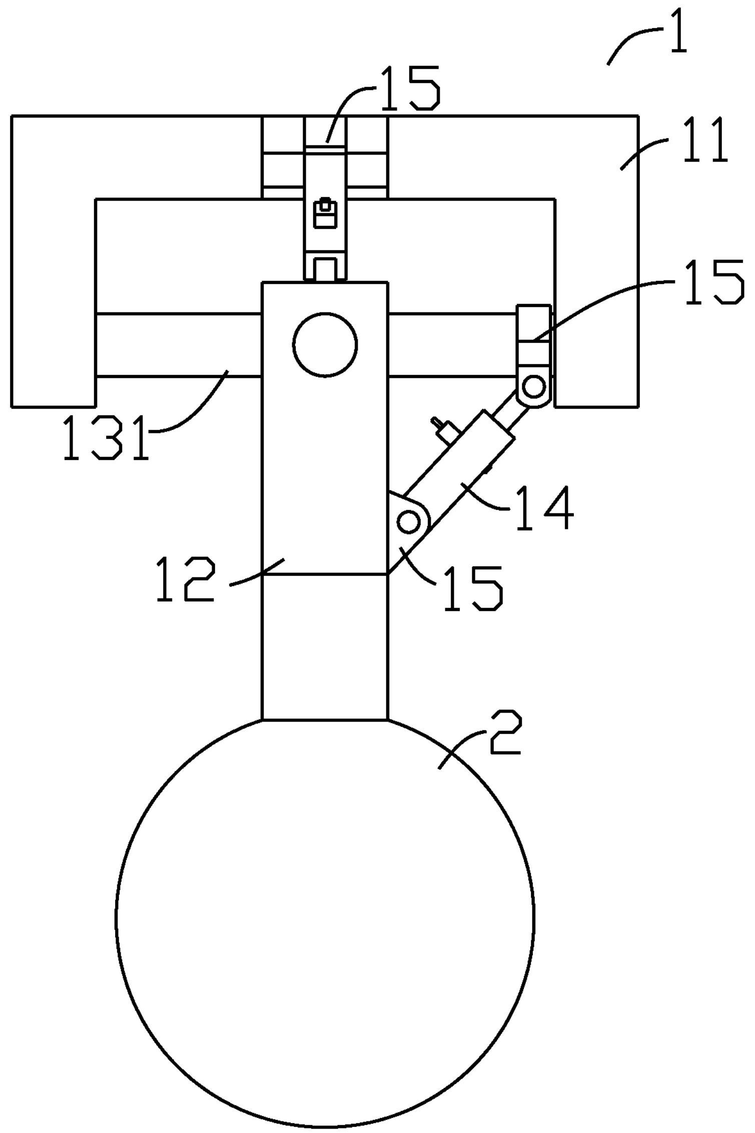
FIG. 3 shows the structure as shown in FIG. 1 from other viewing angle.

Referring to FIGS. 1 to 3, in an embodiment, the rotating shaft 13 comprises at least a first rotating shaft 131 and a second rotating shaft 132, the first rotating shaft 131 and the second rotating shaft 132 are perpendicular to each other and are connected to each other. The first rotating shaft 131 and the second rotating shaft 132 may be intersecting and perpendicular, or may be oppositely perpendicular. The first connection portion 11 is rotatably connected to the first rotating shaft 131 and the second connection portion 12 is rotatably connected to the second rotating shaft 132, so that the first connection portion 11 is connected to and can rotate relative to the second connection portion 12. When the locking mechanism 14 is in the unlocked state, the second connection portion 12 can rotate about the first rotating shaft 131 and/or the second rotating shaft 132, and the second connection portion 12 is connected to the medical device 2, so that the medical device 2 can rotate about the first rotating shaft 131 and/or the second rotating shaft 132, so as to adjust the position of the medical device 2. Moreover, in a preferred embodiment, the first rotating shaft 131 is connected vertically to the second rotating shaft 132 to enable the medical device 2 to be adjusted in a front-to-back, left-to-right position. Compared to the first rotating shaft 131 and the second rotating shaft 132 intersecting at a different angle, such connection enlarges the range of adjusting the position of the medical device 2 along its circumferential direction. Even so, the first rotating shaft 131 and the second rotating shaft 132 may also intersect at other angles.

When the medical device 2 is adjusted to the vertical state, a plane formed by the first rotating shaft 131 and the second rotating shaft 132 may be perpendicular to the vertical direction, or may intersect the vertical direction at other angles.

Referring to FIG. 1 and FIG. 2, in an embodiment, a locking mechanism 14 is disposed between the first connection portion 11 and the second rotating shaft 132. One end of the locking mechanism 14 is rotatably connected to the first connection portion 11, and the other end of the locking mechanism 14 is rotatably connected to the second rotating shaft 132. When the locking mechanism 14 is in the locked state, the locking mechanism 14 can restrict the second connection portion 12 from rotating about the first rotating shaft 131 to restrict the second connection portion 12 from rotating relative to the first connection portion 11, and thereby restrict the rotation of the medical device 2. When the locking mechanism 14 is in the unlocked state, the second rotating shaft 132 can rotate relative to the first connection portion 11 so that the second connection portion 12 can rotate about the first rotating shaft 131 to adjust the position of the medical device 2.

Referring to FIG. 1 and FIG. 3, further, a locking mechanism 14 is also disposed between the second connection portion 12 and the first rotating shaft 131. One end of the locking mechanism 14 is rotatably connected to the second connection portion 12, and the other end of the locking mechanism 14 is rotatably connected to the first rotating shaft 131. When the locking mechanism 14 is in the locked state, the locking mechanism 14 can restrict the second connection portion 12 from rotating about the second rotating shaft 132 to restrict the second connection portion 12 from rotating relative to the first connection portion 11, and thereby restrict the rotation of the medical device 3. When the locking mechanism 14 is in the unlocked state, the second rotating shaft 12 can rotate relative to the first rotating shaft 131 so that the second connection portion 12 can rotate about the second rotating shaft 132 to adjust the position of the medical device 2.

Furthermore, the locking mechanism 14 between the first connection portion 11 and the second rotating shaft 132 and the locking mechanism 14 between the second connection portion 12 and the first rotating shaft 131 can be in an unlocked state or a locked state at the same time, so as to adjust the position of the medical device 2 more quickly.

For example, when the locking mechanism 14 between the first connection portion 11 and the second rotating shaft 132 and the locking mechanism 14 between the second connection portion 12 and the first rotating shaft 131 are both in the unlocked state, the medical device 2 with its own gravity drives the second connection portion 12 to rotate about the first rotating shaft 131 for position adjustment of the medical device 2 along the direction of the second rotating shaft 132. The direction of the second rotating shaft 132 is an axial direction of the second rotating axis 132. And also, the medical device 2 with its own gravity drives the second connection portion 12 to rotate about the second rotating shaft 132 for position adjustment of the medical device 2 along the direction of the first rotating shaft 131, so that the medical device 2 can be quickly adjusted to the vertical state. The direction of the first rotating shaft 131 is an axial direction of the first rotating shaft 131. If only one of the locking mechanisms is in a unlocked state each time, the medical device is only adjusted in one direction and may need to be adjusted several times to reach the vertical state.

Referring to FIGS. 1 to 3, in an embodiment, the first rotating shaft 131, the second rotating shaft 132, the first connection portion 11, and the second connection portion 12 are all connected to hinge bases 15, and locking mechanisms (14) corresponding to the first rotating shaft (131), the second rotating shaft (132), the first connection portion (11) and the second connection portion (12) are rotatably connected to the hinge bases 15. In some embodiments of the present invention, the locking mechanisms 14 are rotatably connected to the first connection portion 11, the second connection portion 12, the first rotating shaft 131 and the second rotating shaft 132 through the hinge bases 15. The hinge bases 15 are fixedly connected to the first connection portion 11 and the second connection portion 12, while the hinge bases 15 are rotatably connected to the first rotating shaft 131 and the second rotating shaft 132, so that when the second connection portion 12 rotates about the first rotating shaft 131, the first rotating shaft 131 rotates relative to the hinge base 15 mounted thereon, and that when the second connection portion 12 rotates about the second rotating shaft 132, the second rotating shaft 132 rotates relative to the hinge base 15 mounted thereon. It is worth mentioning that in other possible embodiments of the present invention, one end of the locking mechanism 14 is connected to the first connection portion 11 through a hinge base 15 and the other end of the locking mechanism 14 is connected to the second connection portion 12 through a hinge base 15, so that the first connection portion 11 and the second connection part 12 can rotate relative to each other.

Figure 4:
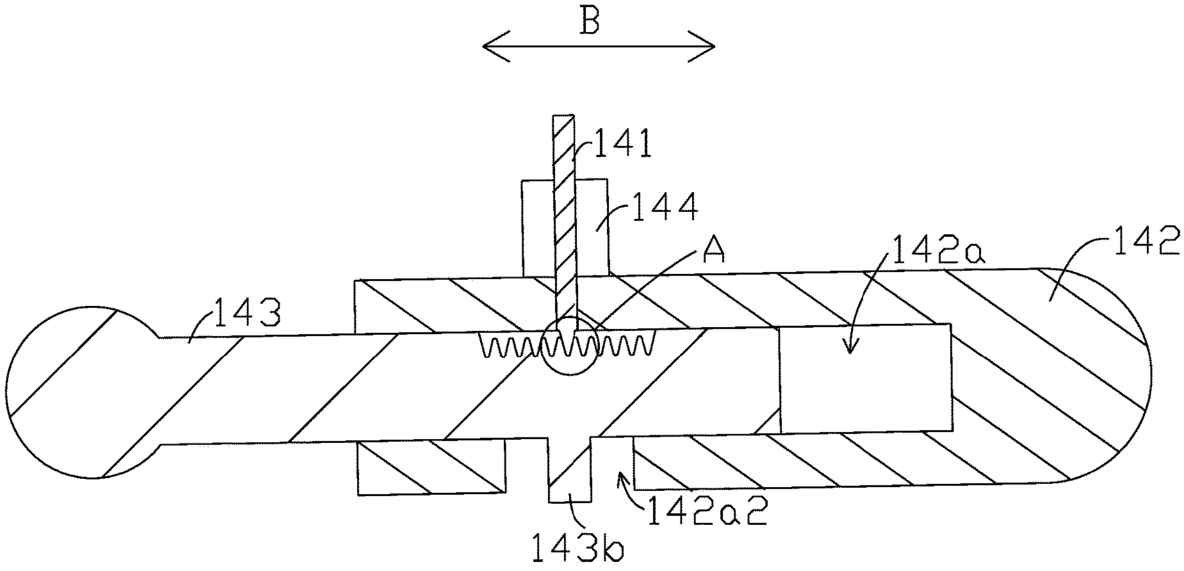
FIG. 4 shows a complete section of a locking mechanism when in a locked state in accordance with the present invention.
Figure 5:
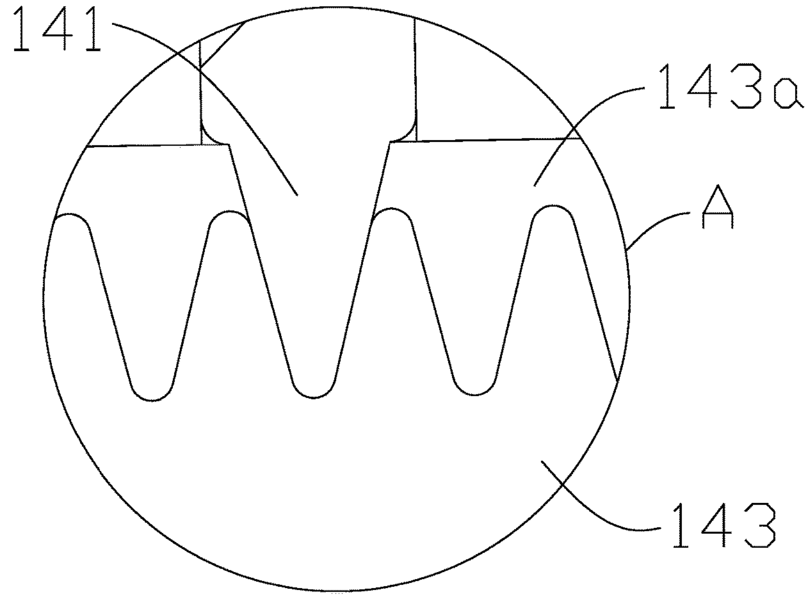
FIG. 5 shows an enlarged view of part A as shown in FIG. 4.
Figure 6:
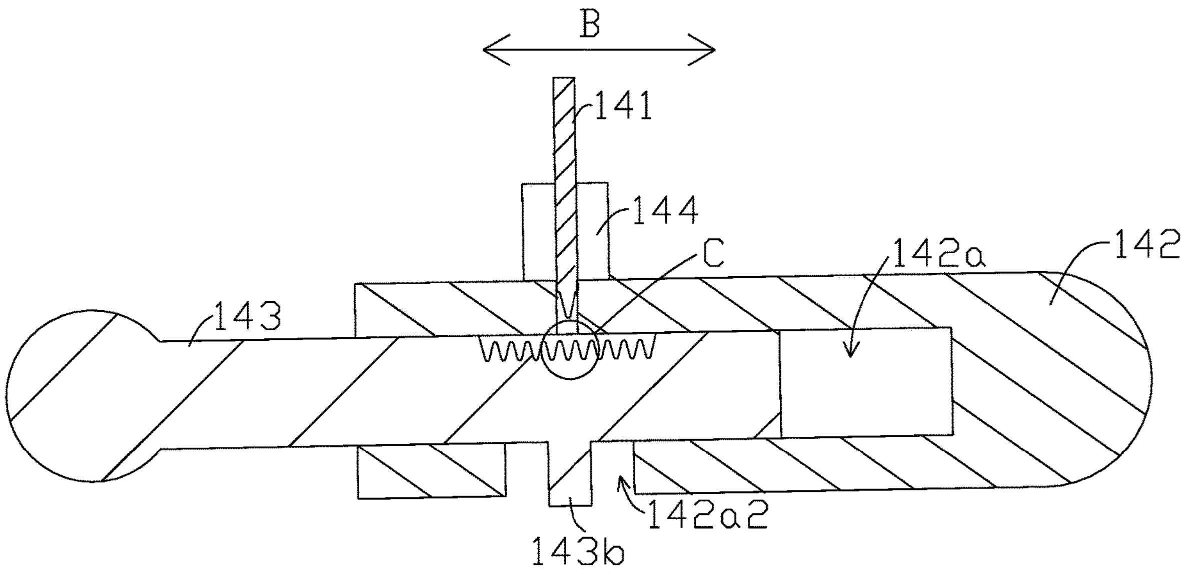
FIG. 6 shows a complete section of a locking mechanism when in a unlocked state in accordance with the present invention.
Figure 7:
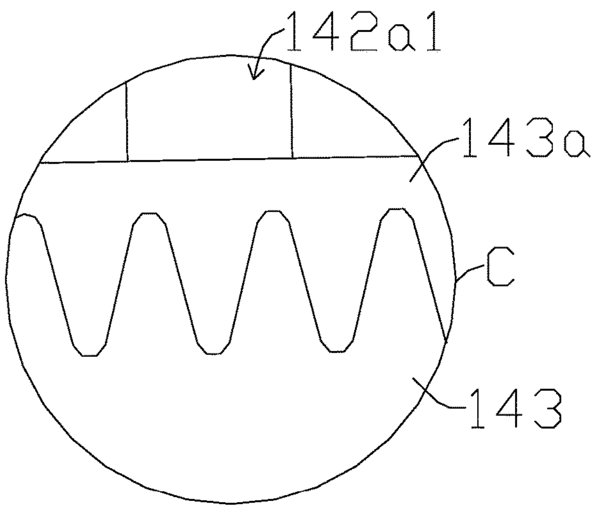
FIG. 7 shows an enlarged view of part C as shown in FIG. 6.

Referring to FIGS. 4 to 6, in a possible design, the locking mechanism 14 comprises a limit portion 141, a first locking portion 142 and a second locking portion 143. One of the first locking portion 142 and the second locking portion 143 is connected to the first connection portion 11 or the second connection portion 12, and the other is connected to the rotating shaft 13. The first locking portion 142 is provided with a holding cavity **142*a*, and at least part of the second locking portion 143 moves along the holding cavity 142*a*, so that the locking mechanism 14 is in an unlocked state. The limit portion 141 is used for limiting a relative movement between the second locking portion 143 and the first locking portion 142, so that the locking mechanism 14 is in a locked state. In some embodiments of the present invention, the second locking portion 143 can move along the holding cavity 142*a* to make a length of the locking mechanism 14 changeable, so that the second connection portion 12 can rotate about the first rotating shaft 131 or the second rotating shaft 132, and at this point, the locking mechanism 14 is in the unlocked state. The second locking portion 143 can also be restricted from moving along the holding cavity 142*a* by the limit portion 141 to maintain the length of the locking mechanism 14, so that the second connection portion 12 is restricted from rotating about the first rotating shaft 131 or the second rotating shaft 132, and at this point, the locking mechanism 14** is in the locked state.

Specifically, when the medical device 2 is in an tilted state relative to the vertical direction, the locking mechanism 14 is controlled to be in the unlocked state, and the medical device 2 can depend on its own gravity to drive the second connection portion 12 to rotate about the first rotating shaft 131 or the second rotating shaft 132, and a certain pushing force or pulling force is applied to the first locking portion 142 or the second locking portion 143 of the locking mechanism 14, so that the second locking portion 143 moves relative to the holding cavity **142*a*, and the second connection portion 12 rotates relative to the first connection portion 11, thereby adjusting the medical device 2 to the vertical state. After the locking mechanism 14 is adjusted to the vertical state and comes to rest, the locking mechanism 14 is controlled to be in the locked state, and the second locking portion 143 is restricted by the limit portion 141 from moving along the holding cavity 142*a* to limit the rotation of the second connection portion 12 relative to the first connection portion 11, so that the medical device 2** can maintain the vertical state.

Referring to FIGS. 4 to 7, in a possible embodiment, a side wall of the holding cavity **142*a* has a through hole 142*a*1. The second locking portion 143 comprises a plurality of locking grooves 143*a* in a side facing the through hole 142*a*1, and the plurality of locking grooves 143*a* are arranged along an axial direction B of the second locking portion 143. The limit portion 141 extends into the holding cavity 142*a* through the through hole 142*a*1 and fits into the locking groove 143*a* so as to limit the relative movement between the second locking portion 143 and the first locking portion 142. In this embodiment, the limit portion 141 is controlled to leave the locking groove 143*a* to enable the second locking portion 143 to move along the holding cavity 142*a*, so that the second connection portion 12 can rotate relative to the first connection portion 11, and the limit portion 141 is controlled to extend into holding cavity 142*a* and fit into one of the locking grooves 143*a*, to restrict the movement of the second locking portion 143 along the holding cavity 142*a* and restrict the rotation of the second connection portion 12 relative to the first connection portion 11**.

The axial direction B of the second locking portion 143 is a direction parallel to a shaft axis of the second locking portion 143.

Further, a cross-sectional area of the locking groove **143*a* gradually decreases in the direction from a groove mouth of the locking groove 143*a* to a bottom of the locking groove 143*a*, and the plurality of locking grooves 143*a* are arranged into a rack structure, and part of the structure of the limit portion 141 that fits into the locking grooves 143*a* corresponds to the locking grooves 143*a*, which facilitates the limit portion 141 to extend into the locking grooves 143*a* and ensures the working reliability of the locking mechanism 14. The shapes of the locking groove 143*a* and the limit portion 141 are not limited to this, and are also feasible as long as they can fit with each other for relative movement between the first locking portion 142 and the second locking portion 143**, which are not be repeated here.

Referring to FIG. 4 and FIG. 6, in a possible embodiment, the locking mechanism 14 further comprises a valve 144, and a stem of the valve 144 is the limit portion 141. The stem is controlled by the valve 144 to move along the through hole **142*a*1, and the stem inserts or leaves the locking groove 143*a*, to get the locking mechanism 14** into the locked state or the unlocked state.

Further, the valve 144 may be a solenoid valve. The solenoid valve is mounted on an outer wall of the first connection portion 142 and can control the movement of the stem along the through hole 142*a*1. When the solenoid valve is open, it controls the stem to move along the through hole 142*a*1 in a direction away from the locking grooves 143*a* to leave the locking grooves 143*a*, causing the locking mechanism 14 to unlock. And when the solenoid valve is closed, the stem moves along the through hole 142*a*1 in a direction close to the locking grooves 143*a* and fits into one of the locking grooves 143*a* to lock the locking mechanism 14. It is worth mentioning that in other possible embodiments, the limit portion 141 and the stem are independent components, and the limit portion 141 can be driven to move by the stem. Also, the valve 144 may be other types, and the structure of the limit portion 141 is not limited in this embodiment.

Referring to FIG. 4 and FIG. 6, in a possible embodiment, the side wall of the holding cavity 142*a* comprises a recess 142*a*2, and the recess 142*a*2 extends in length along the axial direction B of the first locking portion 142. The second locking portion 143 comprises a protrusion 143*b*, at least part of the protrusion 143*b* is located in the recess 142*a*2 and moves in the recess 142*a*2, and two side walls of the recess 142*a*2 along the axial direction B of the first locking portion 142 are for limiting a distance of movement of the protrusion 143*b*. In some embodiments of the present invention, the protrusion 143*b* can move within the recess 142*a*2, and the protrusion 143*b* is fixedly connected to the first locking portion 142, so that the length of the recess 142*a*2 is in a range of movement of the second locking portion 143 relative to the first locking portion 142, to limit the movement distance of the protrusion 143*b*, so as to prevent the second locking portion 143 from moving too much and escaping from the holding cavity 142*a* of the first locking portion 142. Further, the length of the recess 142*a*2 is the rotation range of the medical device 2, ensuring that the rotation angle of the medical device 2 is within a controllable range, and reducing the damage and injury to the device or to personnel caused by an excessive rotation angle of the medical device 2.

Referring to FIG. 4 and FIG. 6, in a possible embodiment, along the axial direction B of the first locking portion 142, the recess 142*a*2 has a size less than or equal to a length of arrangement of the plurality of locking grooves 143*a*, so as to prevent the second locking portion 143 from moving too far, which may cause the limit portion 141 to have no fitted locking groove 143*a* after extending into the holding cavity 142*a*, and to collide with the side wall of the second locking portion 143 and fail to lock the locking mechanism 14.

Further, the locking mechanism may also be in other structural forms, such as a hydraulic cylinder, an air cylinder, etc. Taking the hydraulic cylinder as an example, a piston rod of the hydraulic cylinder can move along a cylinder body of the hydraulic cylinder, and the cylinder body and the piston rod are respectively connected to the first connection portion or the second connection portion and the rotating shaft.

The person skilled in the art realizes that the present invention by no means is limited to the preferred embodiments described above. On the contrary, many modifications and variations are possible within the scope of the appended claims. Any modifications, equivalent substitutions, improvements, etc. made within the spirit and principles of this disclosure are intended to be included within the scope of the present invention.

The invention claimed is:

1. An adjustment device, for adjusting a position of a medical device (2), the adjustment device (1) comprises:

a first connection portion (11) for hoisting the adjustment device (1);

a second connection portion (12) for connecting the medical device (2);

a rotating shaft (13), wherein the first connection portion (11) and the second connection portion (12) are rotatably connected through the rotating shaft (13), so that the first connection portion (11) and the second connection portion (12) rotate relative to each other; and a locking mechanism (14);

wherein the locking mechanism (14) comprises a locked state and an unlocked state, and in the unlocked state, the first connection portion (11) and/or the second connection portion (12) rotate relative to the rotating shaft (13), to adjust the medical device (2) to a vertical position; in the locked state, the locking mechanism (14) restricts the first connection portion (11) and/or the second connection portion (12) to rotate relative to the rotating shaft (13), to maintain the medical device (2) in a vertical state, wherein the rotating shaft (13) comprises at least a first rotating shaft (131) and a second rotating shaft (132), and the first rotating shaft (131) and the second rotating shaft (132) are perpendicular to and connected to each other;

the first connection portion (11) is rotatably connected to the first rotating shaft (131), and the second connection portion (12) is rotatably connected to the second rotating shaft (132).

2. The adjustment device of claim 1, wherein the locking mechanism (14) comprises a limit portion (141), a first locking portion (142), and a second locking portion (143); wherein one of the first locking portion (142) and the second locking portion (143) is connected to the first connection portion (11) or the second connection portion (12), and the other is connected to the rotating shaft (13);

the first locking portion (142) is provided with an holding cavity (142*a*), and at least part of the second locking portion (143) moves along the holding cavity (142*a*), so that the locking mechanism (14) is in the unlocked state;

the limit portion (141) is for limiting a relative movement between the second locking portion (143) and the first locking portion (142), so that the locking mechanism (14) is in the locked state.

3. The adjustment device of claim 2, wherein a side wall of the holding cavity (142*a*) has a through hole (142*a*1);

the second locking portion (143) comprises a plurality of locking grooves (143*a*) in a side facing the through hole (142*a*1), and the plurality of locking grooves (143*a*) are arranged along an axial direction (B) of the second locking portion (143);

the limit portion (141) extends into the holding cavity (142*a*) through the through hole (142*a*1) and fits into the locking groove (143*a*) to limit a relative movement between the second locking portion (143) and the first locking portion (142).

4. The adjustment device of claim 2, wherein the locking mechanism (14) further comprises a valve (144), and a stem of the valve (144) is the limit portion (141).

5. The adjustment device of claim 2, wherein the side wall of the holding cavity (142*a*) comprises a recess (142*a*2), and the recess (142*a*2) extends in length along an axial direction (B) of the first locking portion (142);

the second locking portion (143) comprises a protrusion (143*b*), at least part of the protrusion (143*b*) is located in the recess (142*a*2) and moves in the recess (142*a*2), and two side walls of the recess (142*a*2) along the axial direction (B) of the first locking portion (142) are for limiting a distance of movement of the protrusion (143*b*).

6. The adjustment device of claim 5, wherein along the axial direction (B) of the first locking portion (142), a size of the recess (142*a*2) is less than or is equal to a length of arrangement of the plurality of locking grooves (143*a*).

7. The adjustment device of claim 1, wherein the locking mechanism (14) is disposed between the first connection portion (11) and the second rotating shaft (132);

two ends of the locking mechanism (14) are rotatably connected to the first connection portion (11) and the second rotating shaft (132), respectively;

the second connection portion (12) is restricted from rotating about the first rotating shaft (131) when the locking mechanism (14) is in the locked state, and the second rotating shaft (132) rotates relative to the first connection portion (11) to allow the second connection portion (12) to rotate about the first rotating shaft (131) when the locking mechanism (14) is in the unlocked state.

8. The adjustment device of claim 1, wherein the locking mechanism (14) is disposed between the second connection portion (12) and the first rotating shaft (131);

two ends of the locking mechanism (14) are rotatably connected to the second connection portion (12) and the first rotating shaft (131), respectively;

the second connection portion (12) is restricted from rotating about the second rotating shaft (132) when the locking mechanism (14) is in the locked state, and the second connection portion (12) rotates relative to the first rotating shaft (131) to allow the second connection portion (12) to rotate about the second rotating shaft (132) when the locking mechanism (14) is in the unlocked state.

9. The adjustment device of claim 1, wherein the first rotating shaft (131), the second rotating shaft (132), the first connection portion (11) and the second connection portion (12) are all connected to hinge bases (15), and locking mechanisms (14) corresponding to the first rotating shaft (131), the second rotating shaft (132), the first connection portion (11) and the second connection portion (12) are rotatably connected to the hinge bases (15).

10. A medical system, comprises:

a medical device (2); and an adjustment device (1), wherein the adjustment device (1) is the adjustment device (1);

wherein the adjustment device (1) is connected to the medical device (2) for adjusting a position of the medical device (2);

wherein the adjustment device (1) comprises:

a first connection portion (11) for hoisting the adjustment device (1);

a second connection portion (12) for connecting the medical device (2);

a rotating shaft (13), wherein the first connection portion (11) and the second connection portion (12) are rotatably connected through the rotating shaft (13), so that the first connection portion (11) and the second connection portion (12) rotate relative to each other; and a locking mechanism (14);

wherein the locking mechanism (14) comprises a locked state and an unlocked state, and in the unlocked state, the first connection portion (11) and/or the second connection portion (12) rotate relative to the rotating shaft (13), to adjust the medical device (2) to a vertical position; in the locked state, the locking mechanism (14) restricts the first connection portion (11) and/or the second connection portion (12) to rotate relative to the rotating shaft (13), to maintain the medical device (2) in a vertical state, wherein the rotating shaft (13) comprises at least a first rotating shaft (131) and a second rotating shaft (132), and the first rotating shaft (131) and the second rotating shaft (132) are perpendicular to and connected to each other;

the first connection portion (11) is rotatably connected to the first rotating shaft (131), and the second connection portion (12) is rotatably connected to the second rotating shaft (132).

11. The medical system of claim 10, wherein the locking mechanism (14) comprises a limit portion (141), a first locking portion (142), and a second locking portion (143); wherein one of the first locking portion (142) and the second locking portion (143) is connected to the first connection portion (11) or the second connection portion (12), and the other is connected to the rotating shaft (13);

the first locking portion (142) is provided with an holding cavity (142*a*), and at least part of the second locking portion (143) moves along the holding cavity (142*a*), so that the locking mechanism (14) is in the unlocked state;

the limit portion (141) is for limiting a relative movement between the second locking portion (143) and the first locking portion (142), so that the locking mechanism (14) is in the locked state.

12. The medical system of claim 11, wherein a side wall of the holding cavity (142*a*) has a through hole (142*a*1);

the second locking portion (143) comprises a plurality of locking grooves (143*a*) in a side facing the through hole (142*a*1), and the plurality of locking grooves (143*a*) are arranged along an axial direction (B) of the second locking portion (143);

the limit portion (141) extends into the holding cavity (142*a*) through the through hole (142*a*1) and fits into the locking groove (143*a*) to limit a relative movement between the second locking portion (143) and the first locking portion (142).

13. The medical system of claim 11, wherein the locking mechanism (14) further comprises a valve (144), and a stem of the valve (144) is the limit portion (141).

14. The medical system of claim 11, wherein the side wall of the holding cavity (142*a*) comprises a recess (142*a*2), and the recess (142*a*2) extends in length along an axial direction (B) of the first locking portion (142);

the second locking portion (143) comprises a protrusion (143*b*), at least part of the protrusion (143*b*) is located in the recess (142*a*2) and moves in the recess (142*a*2), and two side walls of the recess (142*a*2) along the axial direction (B) of the first locking portion (142) are for limiting a distance of movement of the protrusion (143*b*).

15. The medical system of claim 14, wherein along the axial direction (B) of the first locking portion (142), a size of the recess (**142*a*2) is less than or is equal to a length of arrangement of the plurality of locking grooves (143*a***).

16. The medical system of claim 10, wherein the locking mechanism (14) is disposed between the first connection portion (11) and the second rotating shaft (132);

two ends of the locking mechanism (14) are rotatably connected to the first connection portion (11) and the second rotating shaft (132), respectively;

the second connection portion (12) is restricted from rotating about the first rotating shaft (131) when the locking mechanism (14) is in the locked state, and the second rotating shaft (132) rotates relative to the first connection portion (11) to allow the second connection portion (12) to rotate about the first rotating shaft (131) when the locking mechanism (14) is in the unlocked state.

17. The medical system of claim 10, wherein the locking mechanism (14) is disposed between the second connection portion (12) and the first rotating shaft (131);

two ends of the locking mechanism (14) are rotatably connected to the second connection portion (12) and the first rotating shaft (131), respectively;

the second connection portion (12) is restricted from rotating about the second rotating shaft (132) when the locking mechanism (14) is in the locked state, and the second connection portion (12) rotates relative to the first rotating shaft (131) to allow the second connection portion (12) to rotate about the second rotating shaft (132) when the locking mechanism (14) is in the unlocked state.

18. The medical system of claim 10, wherein the first rotating shaft (131), the second rotating shaft (132), the first connection portion (11) and the second connection portion (12) are all connected to hinge bases (15), and locking mechanisms (14) corresponding to the first rotating shaft (131), the second rotating shaft (132), the first connection portion (11) and the second connection portion (12) are rotatably connected to the hinge bases (15).

* * * * *